(12) United States Patent
Riemenschneider

(10) Patent No.: US 10,493,196 B2
(45) Date of Patent: Dec. 3, 2019

(54) METHOD OF DRAINING A DEVICE FOR EXTRACORPOREAL BLOOD TREATMENT

(71) Applicant: B. BRAUN AVITUM AG, Melsungen (DE)

(72) Inventor: Heiko Riemenschneider, Wagenfurth (DE)

(73) Assignee: B. Braun Avitum AG (DE)

( * ) Notice: Subject to any disclaimer, the term of this patent is extended or adjusted under 35 U.S.C. 154(b) by 362 days.

(21) Appl. No.: 15/480,899

(22) Filed: Apr. 6, 2017

(65) Prior Publication Data

US 2017/0296733 A1    Oct. 19, 2017

(30) Foreign Application Priority Data

Apr. 15, 2016   (DE) ................. 10 2016 107 026

(51) Int. Cl.
*A61M 1/36* (2006.01)
*A61M 1/16* (2006.01)
*A61M 1/10* (2006.01)

(52) U.S. Cl.
CPC ............ *A61M 1/3621* (2013.01); *A61M 1/10* (2013.01); *A61M 1/1086* (2013.01);
(Continued)

(58) Field of Classification Search
CPC .............. A61M 1/3621; A61M 1/3624; A61M 1/1601; A61M 1/365; A61M 1/3652;
(Continued)

(56) References Cited

U.S. PATENT DOCUMENTS

| 4,770,769 A | 9/1988 | Schael | |
| 2010/0087772 A1* | 4/2010 | Gronau | A61M 1/3643 604/6.09 |
| 2012/0265117 A1 | 10/2012 | Fava et al. | |

FOREIGN PATENT DOCUMENTS

| DE | 10245619 A1 | 3/2004 |
| EP | 1161271 B1 | 12/2001 |
| WO | 2008028579 A1 | 3/2008 |

OTHER PUBLICATIONS

European Search Report with English language translation for Application No. 17 165 300.9, dated Aug. 21, 2017, 14 pages.
(Continued)

*Primary Examiner* — Philip R Wiest
(74) *Attorney, Agent, or Firm* — RatnerPrestia

(57) ABSTRACT

A method of draining a device for extracorporeal blood treatment, wherein the device comprises a dialyzer which is divided by means of a membrane into a first chamber and a second chamber, an arterial line connected to a blood inlet of the first chamber, a venous line connected to a blood outlet of the first chamber, a dialysis fluid line for fresh dialysis fluid connected to a dialysis fluid inlet of the second chamber and a dialysis fluid line for used dialysis fluid connected to a dialysis fluid outlet of the second chamber, a blood pump disposed in the arterial line, a venous expansion chamber disposed in the venous line and an air detector unit downstream of the venous expansion chamber, and wherein the method comprises the following steps of: connecting a patient-side port of the arterial line to a patient-side port of the venous line; generating a negative pressure in the second chamber; operating the blood pump in a first direction and draining the arterial and venous lines in the first direction via the membrane and the second chamber; and stopping the blood pump and draining the arterial and venous lines in a
(Continued)

second direction opposed to the first direction via the membrane and the second chamber.

18 Claims, 2 Drawing Sheets

(52) U.S. Cl.
CPC ........ *A61M 1/1601* (2014.02); *A61M 1/3626* (2013.01); *A61M 2205/15* (2013.01)
(58) Field of Classification Search
CPC .... A61M 1/10; A61M 1/1086; A61M 1/3626; A61M 1/3629; A61M 1/363; A61M 1/3643; A61M 2205/07; A61M 2205/15; A61M 2205/705
See application file for complete search history.

(56) References Cited

OTHER PUBLICATIONS

German Search Report for German Application No. 10 2016 107 026.2, dated Oct. 26, 2016, including English translation, 17 pages.
International Preliminary Report on Patentability and Written Opinion for International Application No. PCT/EP2007/007505, dated Apr. 22, 2009, 6 pages.

\* cited by examiner

— METHOD OF DRAINING A DEVICE FOR EXTRACORPOREAL BLOOD TREATMENT

CROSS REFERENCE TO RELATED APPLICATIONS

This application claims priority to German application DE 10 2016 107 026.2 filed Apr. 15, 2016, the contents of such application being incorporated by reference herein.

FIELD OF THE INVENTION

The invention relates to a method of draining a device for extracorporeal blood treatment and especially relates to a method of automated and complete draining of both a hose system and a dialyzer device for a device for extracorporeal blood treatment after the return of blood via the dialyzer device.

BACKGROUND OF THE INVENTION

A known device for extracorporeal blood treatment comprises at least one treatment unit such as a dialyzer and, respectively, a dialyzer device, or a filter, ultra-filter or plasma filter of a different filter unit having a semipermeable membrane for separating the treatment unit into two chambers. An extracorporeal blood circulation enables blood taken from a patient to flow through the first chamber back to the patient. At the same time, in the opposite direction thereto a dialysis fluid (treatment fluid) flows through an appropriately designed circuit via the second chamber. The known device moreover includes a dialysis fluid line for fresh dialysis fluid connected to the second chamber on the inlet side and a dialysis fluid line for used dialysis fluid connected to the second chamber on the outlet side.

After the end of therapy and the return of blood, the user of the known device usually is confronted with the problems of an appropriate draining of the (fluid) system of the device. With respect to draining, so far merely a cartridge possibly used during therapy, for example a bicarbonate cartridge, as well as the dialyzer device (the dialyzer) on the water side have been supported so far. The blood side, on the other hand, usually remains filled. This involves risks of infection and unnecessarily increases the amount of weight of disposables such as of the dialyzer and the blood hose system. Moreover, even when the user exercises utmost care, regularly blood residues and/or residual components of fresh and/or used dialysis fluid reach the surrounding bottom surface and/or to the device and, respectively, the machine itself.

Known methods and/or devices in general include flushing of the hose system with a liquid such as e.g. saline solution or dialysis fluid so as to remove residual blood and draining of the flushing liquid through a specific outlet.

As a rule, a user is provided with description and training as to how a device or a machine for extracorporeal blood treatment has to be dismounted again after therapy. Accordingly, merely the water side of the system and the cartridge are drained, however. It is not taken into consideration, however, in which way blood-side residual amounts in the blood hose system have to be treated. However, residual or waste amounts which are annually accumulating on the blood side and have to be disposed cost-intensively as special waste are considerable.

Hence there is a need of a solution which also assists the user equally fully automatically in draining (on the blood side) the hose system including the dialyzer just as in draining the system and the cartridge (on the water side).

SUMMARY OF THE INVENTION

Consequently, the object underlying the invention is to provide a method of draining a device for extracorporeal blood treatment which assists a user of the device during a draining cycle after the end of therapy by an automated process which can be easily and safely handled.

Moreover, the invention is intended to provide a simple and largely fully automatic process for completely draining the hose system including the dialyzer after blood return via the dialyzer.

Furthermore, the invention is intended to minimize risks of infection and to reduce accumulating amounts of waste in a cost-saving manner.

This object is achieved, according to aspects of the invention, by a method of draining a device for extracorporeal blood treatment comprising the features of the independent claims. Advantageous further developments of the invention are the subject matter of the dependent claims.

Underlying the invention is a general idea of automatically draining also the blood side including existing residual amounts in the dialyzer using the dialyzer membrane and with the aid of level control, alternatively a manually effectuated pressure support, i.e. to provide a process with which in a device for extracorporeal blood treatment residual amounts can be flushed in a way aided by software and/or hardware in the hose system thereof utilizing the dialyzer membrane with support of the level control and/or manual pressure support of the pressure sensors and of the blood pump for fully automatic draining of the blood side including all chambers and of the dialyzer after the end of therapy.

When the user has returned the blood to a patient at the end of therapy, he/she turns to the device again. For example, on the device side he/she then has a "drain system" option activatable by pressing a button, touching the screen or the like which is tantamount to an instruction to the operator to short-circuit the arterial and venous ports and to confirm the respective operation. Upon activating said option, one port after the other of the device is pressurized via level control, the blood pump works at a predetermined delivery rate, for example 100 ml/min, negative pressure is generated on the dialysis fluid side or else on the water side and all residual amounts of fluid are drained via the dialyzer and, respectively, via the membrane thereof from the blood side toward the water side. After few minutes, for example 3 minutes, the entire system including the dialyzer is drained and the user may remove, respectively dismount, it as usual and prepare the device for subsequent treatment again.

Accordingly, a significant reduction of the operating cost and decrease of accumulating amounts of special waste can be achieved. When also the blood side of a dialysis machine is drained, another 200 to 350 ml of residual amount to be disposed of as special waste per treatment are avoidable. For each dialysis machine an amount of special waste accumulating each year ranges from 0.2 to 0.35 t. Assuming the costs of disposal for special waste from dialysis machines and dialysis treatments to be 350 Euros per ton of special waste, the cost reduction potential for the number of the total machines in use is considerable.

In detail, the object is achieved by a method of draining a device for extracorporeal blood treatment, wherein the device includes at least an arterial port, a venous port, a dialyzer device, a blood pump, an air detector, a level control unit and a venous expansion chamber, and wherein the method comprises the steps of; connecting at least the arterial port and the venous port of the device; generating a water-side negative pressure; draining the fluid-carrying lines of the device via the membrane of the dialyzer device in a first direction toward the dialyzer, wherein during draining in the first direction the blood pump is kept in operation; and draining the fluid-carrying lines of the device via the membrane of the dialyzer device in a second direction toward the dialyzer which is opposed to the first direction, wherein during draining in the second direction the blood pump is stopped and during draining in the first direction and during draining in the second direction a level control unit is kept in operation.

Preferably, the level control unit used is a level control pump which is configured to provide level control at least in the venous expansion chamber.

Preferably, during draining in the first direction and during draining in the second direction, arterial and/or venous fluid discharges as well as a fluid discharge from the venous expansion chamber can be assisted by manual pressurization.

Preferably, manual pressurization is carried out by opening pressure sensor ports and/or disconnecting at least one inlet.

Preferably, starting from a point in time when the occurrence of air in the air detector is detected, a number of head revolutions of the blood pump is counted, wherein a predetermined delivery volume per revolution is associated with one head revolution depending on a delivery constant.

Preferably, a switch-off time of the blood pump based on a preset flushing amount and the counted number of head revolutions of the blood pump is established, wherein at the established time of switch-off the operation of the blood pump is stopped and a change is made from draining in the first direction to draining in the second direction.

Preferably, during draining in a second direction after a predetermined period of time a negative pressure is built up also on the blood side of the dialyzer device.

Advantageously, the blood-side negative pressure can be measured at the port of a venous pressure sensor.

Preferably, upon detecting a predetermined blood-side negative pressure, the fluid-carrying lines of the device are closed off on the water side, a pump unit in a drain for used dialysis fluid is stopped and a user is informed about the end of the blood-side draining of the device.

Preferably, the transmembrane pressure is calculated and the draining cycle is interrupted, when the calculated transmembrane pressure exceeds a predetermined limit.

Preferably, the membrane of the dialyzer device is monitored with a blood leakage detecting means in the drain for used dialysis fluid with respect to the occurrence of a rupture.

BRIEF DESCRIPTION OF THE DRAWINGS

The invention is best understood from the following detailed description when read in connection with the accompanying drawings. Included in the drawings are the following figures.

DETAILED DESCRIPTION OF THE PREFERRED EMBODIMENTS

Figure 1:
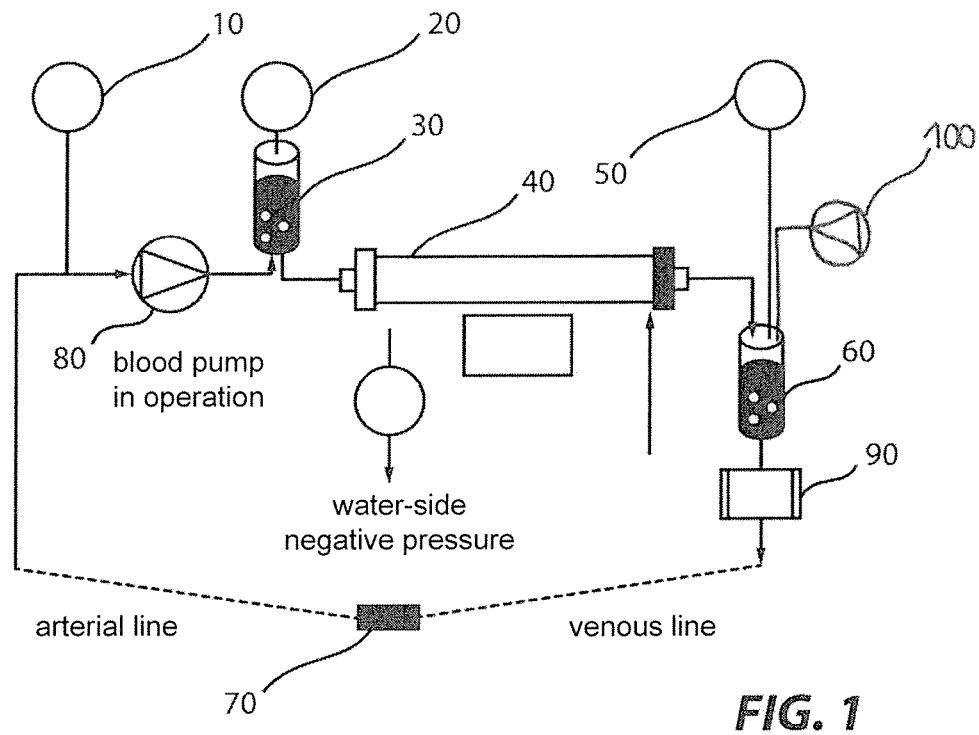
FIG. 1 schematically shows a first section of a cycle in the method of draining a device for extracorporeal blood treatment according to an embodiment.

In the following description of figures like or equally acting elements and/or components may be designated equally and/or by like reference numerals in individual figures and advantageously are not redundantly described. In cases where a subsequent embodiment functionally corresponds to at least a preceding one, i.e. corresponding functions, arrangements and/or process or operating cycles are equally comprised, only differences will advantageously be discussed.

A device for extracorporeal blood treatment such as a dialysis machine for purifying a patient's blood, if e.g. his/her renal function is limited or stopped, includes a dialyzer through which, on the one hand, the patient's blood to be purified and, on the other hand, a dialysis fluid or dialysis solution preferably flows according to the counter flow principle, with particular dissolved substances (e.g. urea) being transferred from the blood to the dialysis fluid.

The system, the structure, the components and the functioning of the afore-mentioned device for extracorporeal blood treatment, which may especially be a dialysis device or a dialysis machine, are basically known per se and therefore are incorporated here and will not be further described.

Figure 2:
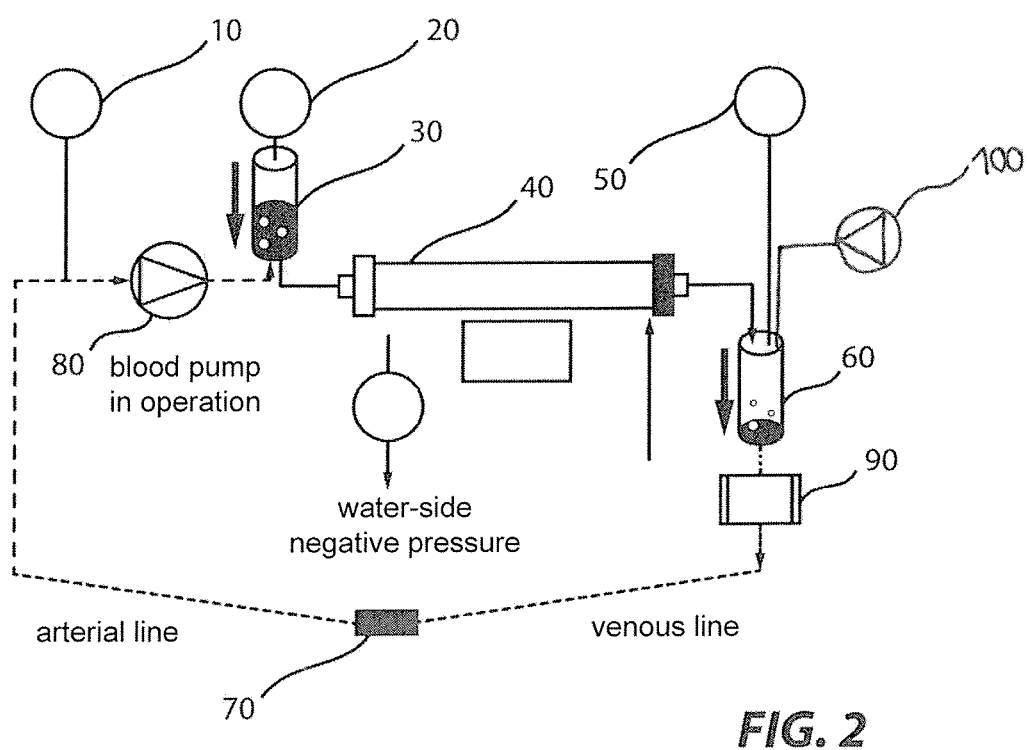
FIG. 2 schematically shows a second section of a cycle in the method of draining a device for extracorporeal blood treatment according to the embodiment.
Figure 3:
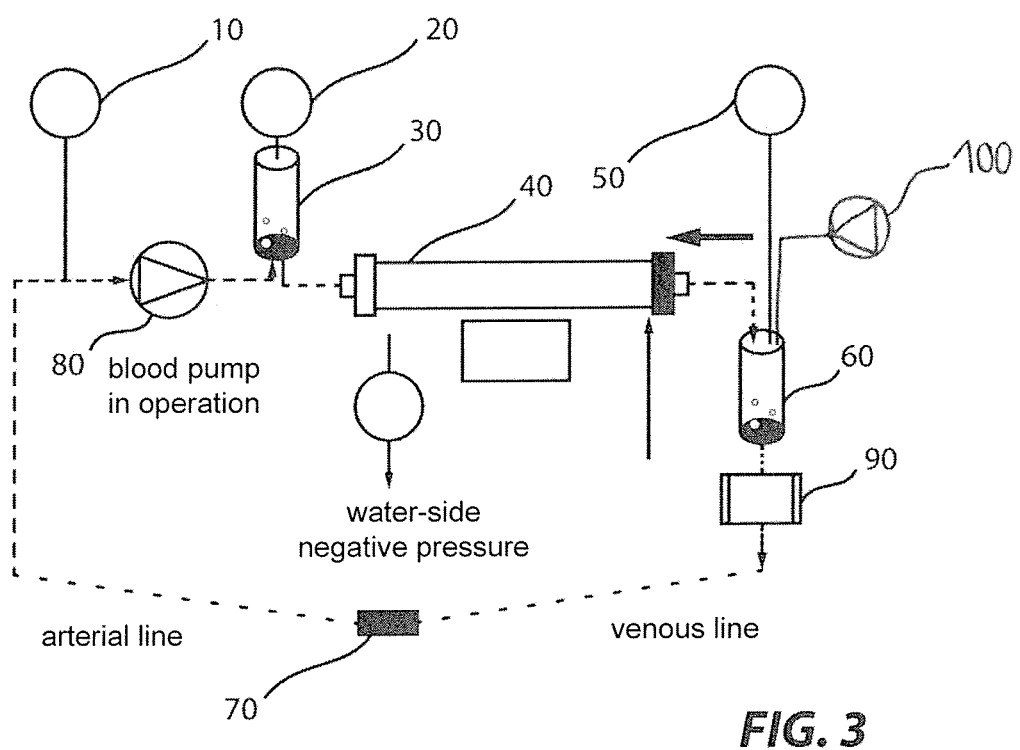
FIG. 3 schematically shows a third section of a cycle in the method of draining a device for extracorporeal blood treatment according to the embodiment.

FIGS. 1 to 3 schematically illustrate first, second and third sections of a cycle in the method of draining a device for extracorporeal blood treatment according to an embodiment. It is noted that FIGS. 1 to 3 refer to the blood side of the device, i.e. the schematically illustrated fluid lines are blood-guiding.

In accordance with FIGS. 1 to 3, a system to be drained by the method of draining a fluid-carrying system of a device for extracorporeal blood treatment such as a dialysis device or a dialysis machine comprises fluid-carrying connecting lines or hose lines which open into at least one arterial port and at least one venous port.

In an arterial fluid line a dialyzer 40 including a dialyzer membrane (not shown), an arterial pressure sensor 10, a blood pump 80, a first (arterial) expansion chamber (bubble chamber, bubble separator) 30 upstream of the dialyzer 40, a pressure sensor 20 at the first expansion chamber 30, a second (venous) expansion chamber (bubble chamber, bubble separator) 60 downstream of the dialyzer 40, a venous pressure sensor 50 at the second expansion chamber 60 and an air detector 90 are arranged. A connecting device (adapter) 70 is provided and arranged for connecting in a fluid-permeable manner and, respectively, short-circuiting an arterial port and a venous port of the fluid or hose system of the device.

Hereinafter the cycle in the method of draining a device for extracorporeal blood treatment according to the present embodiment will be described in greater detail.

When the user of the device for extracorporeal blood treatment has returned the blood to a patient at the end of therapy, he/she turns to the device again. If present, at this point in time a (bicarbonate) cartridge (not shown) may have been drained already. Upon actuating a selector, for example a key, a switch or a touch-sensitive field on a screen-aided user interface, the device is turned into an operating cycle "drain system".

The user now manually joins the arterial and venous ports of the blood hose system with the connector device 70 which may be a (hose or port) adapter, for example, i.e. connects them to be fluid-carrying and confirms the draining on the device with the selector ("drain system" key). It is noted that the two ports of the blood hose system remain connected with the connector device 70 until the draining cycle is completed.

On the device side, at first a (water-side) negative pressure is built up on the dialysis fluid side, preferably e.g. approx. 500 mm Hg, measurable by an appropriately disposed sensor, for example pressure sensor, using a dialysis fluid pump (not shown) which is preferably arranged in the drain of the used dialysis fluid and using proper valve switching. The blood pump 80 starts to operate at a rotational speed of e.g. 50 1/min. A level control pump 100 now lowers the level in the second (venous) expansion chamber 60. The level in said second expansion chamber 60 is thus appropriately lowered until air (air bubbles) is/are detected at the air detector 90. When air or air bubbles is/are detected at the air detector 90 for the first time, now the number of head revolutions at the blood pump 80 (delivery constant) is counted (for example 12.3 ml fluid delivery per revolution of the blood pump 80 are added up).

The amount of fluid present in the short-circuited blood hose system is discharged, on the one hand, due to the pump pressure of the blood pump 80 and, on the other hand, due to the negative pressure prevailing on the water side, from the venous line via the connector device 70, the arterial line, the first chamber of the dialyzer 40, the membrane and the second chamber of the dialyzer 40 to the water side. Accordingly, also the level in the first (arterial) expansion chamber 30 drops (FIG. 2). The operation of the blood pump 80 is continued, i.e. the blood pump 80 is continued being kept in operation, until, up to an intake of the dialyzer 4, the system is filled with air and drained from flushing residues.

Appropriate flushing amounts are dependent on the hose system and can be adjusted by the user. The device calculates, with a known delivery constant, e.g. 12.3 ml/head revolution of the blood pump 80, a switch-off time of the blood pump 80 based on each set flushing amount and the number of the head revolutions of the blood pump 80. When the set flushing amount is reached, the operation of the blood pump 80 is stopped, i.e. the blood pump stops (FIG. 3).

The venous pressure sensor 50 is continued to be pressurized, however, due to the continued operation of the level control pump 100 so that the system starts to drain against the typical flow direction (first direction) back from the venous pressure sensor 50 toward the dialyzer 40 (second direction opposite to the first direction).

After a short period of time, which is approximately one minute in the present embodiment, the operation of the level control pump 100 is stopped, too. Few seconds later, in the present embodiment after approx. 10 seconds, negative pressure is built up also on the blood side. Said negative pressure can be measured on the blood side by the venous pressure sensor 50, for example.

Now valves (not shown) shut off the water side of the device, the dialysis fluid pump is stopped and information or a message that the system draining on the blood side is completed is output to the user.

Then the user uncouples the water-side (for example blue) coupling from the dialyzer 40 and confirms this. In this way, then also the water side of the dialyzer 40 is drained. After that, the entire system is drained and may be removed by the user. Subsequently, the device can be prepared for the next treatment in the intended way.

As a feature increasing the safety, in addition the transmembrane pressure (TMP) at the membrane of the dialyzer 40 can be calculated and the drain cycle can be interrupted, if said pressure becomes too high and exceeds a predetermined limit.

As afore-described, in a method of draining a device for extracorporeal blood treatment comprising at least one arterial port and one venous port of a blood hose system, a dialysis device, a blood pump, an air detector, a level control pump and a venous expansion chamber, at least the arterial port and the venous port of the blood hose system are connected. Then a water-side negative pressure is generated and the fluid-carrying lines of the blood hose system are drained via the dialyzer membrane at first in a first direction toward the dialyzer, wherein during draining in the first direction the blood pump is kept in operation, and then equally via the dialyzer membrane in a second direction toward the dialyzer which is opposite to the first direction, wherein during draining in the second direction the blood pump is stopped.

During draining in the first direction toward the dialyzer and during draining in the second direction toward the dialyzer a level control unit 100 may be kept in operation or, alternatively, arterial and/or venous fluid discharges as well as a fluid discharge from the venous expansion chamber may be assisted by manual pressurization. Starting from a point in time when in the air detector occurrence of air is detected, a number of head revolutions of the blood pump is counted, with a predetermined delivery volume for each revolution being associated with one head revolution as a function of a delivery constant. A switch-off time of the blood pump is established on the basis of a preset flushing amount and the counted number of head revolutions of the blood pump, wherein at the established switch-off time the operation of the blood pump is stopped and a change from draining in the first direction toward the dialyzer to the draining in the second direction toward the dialyzer is made. During draining in a second direction, after a predetermined time period a negative pressure which is measurable at the port of a venous pressure sensor is built up also on the blood side of the dialyzer device.

Upon detecting a predetermined blood-side negative pressure, the fluid-carrying lines of the device are closed on the water side, a pump unit in the drain for used dialysis fluid is stopped and a user is informed about the end of the blood-side draining of the device.

For safeguarding reasons, the transmembrane pressure can be calculated and the draining cycle can be interrupted, if the calculated transmembrane pressure exceeds a predetermined limit. Furthermore, the membrane of the dialyzer device can be monitored by means of a blood leakage detector in the drain for used dialysis fluid with respect to the occurrence of a rupture.

It is understood that the invention is not limited to the described embodiment and the modifications thereof but that within the scope of protection defined by the following claims combinations of at least parts of these embodiments, modifications and equivalents may nonetheless be obvious to those skilled in the art.

In one modification, also blood hose systems on devices which include no level control can be drained, for example. In this case, it may be provided that a user assists the arterial and venous discharges and the expansion chamber(s) by opening the pressure sensor ports and by disconnecting the inlets.

It may further be provided to monitor the draining process by the pressure sensors (on the water side and/or on the blood side) in order to increase the safety. Accordingly, an additional limit range for monitoring the dialyzer membrane (membrane protection against rupture at excessive pressure) and for interrupting the draining for safety reasons may be adopted from the therapy, for example. In the case of an occurring rupture of the dialyzer membrane, a blood leakage detector disposed in the drain for used dialysis fluid may be provided to detect, as blood leakage detecting unit, such rupture and to inform the user about the same.

The invention claimed is:

1. A method of draining a device for extracorporeal blood treatment including a dialyzer divided into a first chamber and a second chamber by a membrane, an arterial line connected to a blood inlet of the first chamber, a venous line connected to a blood outlet of the first chamber, a dialysis fluid line for fresh dialysis fluid connected to a dialysis fluid inlet of the second chamber, and a dialysis fluid line for used dialysis fluid connected to a dialysis fluid outlet of the second chamber, a blood pump disposed in the arterial line, a venous expansion chamber disposed in the venous line and an air detector unit downstream of the venous expansion chamber; the method comprising the steps of:

connecting a patient-side port of the arterial line to a patient-side port of the venous line;

generating negative pressure in the second chamber;

operating the blood pump in a first direction to drain the arterial and venous lines in the first direction via the membrane and the second chamber; and stopping the blood pump to drain the arterial and venous lines in a second direction opposed to the first direction via the membrane and the second chamber.

2. The method according to claim 1, wherein the device further includes at least one level control unit, wherein during draining in the first direction and during draining in the second direction the level control unit is kept in operation.

3. The method according to claim 2, wherein the level control unit is a level control pump configured to provide level control at least in the venous expansion chamber.

4. The method according to claim 1, wherein during draining in the first direction and during draining in the second direction at least one of the arterial line connected to the blood inlet of the first chamber or the venous line connected to the blood outlet of the first chamber and the venous expansion chamber are assisted by manual pressurization.

5. The method according to claim 4, wherein manual pressurization is carried out by at least one of opening pressure sensor ports or disconnecting the blood inlet or blood outlet provided on the respective opposite side of the dialyzer.

6. The method according to claim 1, wherein, starting from a point in time when air is detected in the air detector unit, a number of head revolutions of the blood pump is counted, wherein a predetermined delivery volume for each revolution is associated with one head revolution as a function of a delivery constant.

7. The method according to claim 6, further comprising establishing a switch-off time of the blood pump on the basis of a predetermined flushing amount and the counted number of head revolutions of the blood pump, wherein the operation of the blood pump is stopped at the established switch-off time and a change from draining in the first direction to draining in the second direction is made.

8. The method according to claim 1, wherein during draining in a second direction after a predetermined time period a negative pressure is built up also on the blood side of the dialyzer.

9. The method according to claim 6, wherein during draining in a second direction after a predetermined time period a negative pressure is built up also on the blood side of the dialyzer.

10. The method according to claim 8, wherein the blood-side negative pressure is measurable at the port of a venous pressure sensor.

11. The method according to claim 10, wherein upon detecting a predetermined blood-side negative pressure the fluid-carrying lines of the device are shut off on the water side, a pump unit in a drain for used dialysis fluid is stopped and a user is informed about the end of the blood-side draining of the device.

12. The method according to claim 1, wherein the transmembrane pressure is calculated and the draining cycle is interrupted, if the calculated transmembrane pressure exceeds a predetermined limit.

13. The method according to claim 6, wherein the transmembrane pressure is calculated and the draining cycle is interrupted, if the calculated transmembrane pressure exceeds a predetermined limit.

14. The method according to claim 8, wherein the transmembrane pressure is calculated and the draining cycle is interrupted, if the calculated transmembrane pressure exceeds a predetermined limit.

15. The method according to claim 1, wherein the membrane of the dialyzer is monitored by a blood leakage detecting unit in the drain a drain for used dialysis fluid with respect to occurrence of a rupture.

16. The method according to claim 6, wherein the membrane of the dialyzer is monitored by a blood leakage detecting unit in the drain a drain for used dialysis fluid with respect to the occurrence of a rupture.

17. The method according to claim 8, wherein the membrane of the dialyzer is monitored by a blood leakage detecting unit in the drain a drain for used dialysis fluid with respect to the occurrence of a rupture.

18. The method according to claim 12, wherein the membrane of the dialyzer is monitored by a blood leakage detecting unit in the drain a drain for used dialysis fluid with respect to the occurrence of a rupture.

* * * * *

UNITED STATES PATENT AND TRADEMARK OFFICE
CERTIFICATE OF CORRECTION

PATENT NO.         : 10,493,196 B2                                    Page 1 of 1
APPLICATION NO.    : 15/480899
DATED              : December 3, 2019
INVENTOR(S)        : Heiko Riemenschneider It is certified that error appears in the above-identified patent and that said Letters Patent is hereby corrected as shown below:

In Column 8, Claim 15, Line 41, "detecting unit in the drain a drain ..." should read -- detecting unit in a drain ... --

In Column 8, Claim 16, Line 45, "detecting unit in the drain a drain ..." should read -- detecting unit in a drain ... --

In Column 8, Claim 17, Line 49, "detecting unit in the drain a drain ..." should read -- detecting unit in a drain ... --

In Column 8, Claim 18, Line 53, "detecting unit in the drain a drain ..." should read -- detecting unit in a drain ... --

Signed and Sealed this
Thirty-first Day of March, 2020

Andrei Iancu
*Director of the United States Patent and Trademark Office*